(12) United States Patent
Schoenle et al.

(10) Patent No.: US 8,568,354 B2
(45) Date of Patent: Oct. 29, 2013

(54) DEVICES AND METHODS FOR LOW SHEARING LOCAL DELIVERY OF THERAPEUTIC AGENTS TO THE WALL OF A BODILY LUMEN

(75) Inventors: Victor Leo Schoenle, Greenfield, MN (US); Ryan D. Welty, Blaine, MN (US); Kristina Tibesar Jensen, Chaska, MN (US); Cassandra Ann Piippo Svendsen, Hugo, MN (US); Jeffrey A. McBroom, Champlin, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 223 days.

(21) Appl. No.: 13/026,567

(22) Filed: Feb. 14, 2011

(65) Prior Publication Data
US 2012/0035588 A1 Feb. 9, 2012

Related U.S. Application Data

(60) Provisional application No. 61/305,041, filed on Feb. 16, 2010.

(51) Int. Cl.
*A61M 29/00* (2006.01)
(52) U.S. Cl.
USPC ............ 604/101.02; 604/100.01; 604/100.02; 604/101.01; 604/103.01; 604/103.02
(58) Field of Classification Search
USPC ............... 604/96.01, 100.01, 100.02, 101.01, 604/101.02, 102.01, 102.02, 103.01, 103.02
See application file for complete search history.

(56) References Cited

U.S. PATENT DOCUMENTS

| | | |
|---|---|---|
| 3,848,593 A | 11/1974 | Baldwin |
| 5,423,744 A | 6/1995 | Gencheff et al. |
| 5,599,306 A | 2/1997 | Klein et al. |
| 5,611,775 A | 3/1997 | Machold et al. |
| 5,685,847 A | 11/1997 | Barry |
| 5,833,658 A | 11/1998 | Levy et al. |
| 5,899,882 A | 5/1999 | Waksman et al. |
| 6,048,332 A | 4/2000 | Duffy et al. |
| 6,174,327 B1 | 1/2001 | Mertens et al. |
| 6,537,195 B2 | 3/2003 | Forman |
| 6,599,267 B1 | 7/2003 | Ray et al. |
| 6,638,246 B1 | 10/2003 | Naimark et al. |
| 6,645,135 B1 | 11/2003 | Bhat |
| 6,659,996 B1 | 12/2003 | Kaldany |
| 6,716,190 B1 | 4/2004 | Glines et al. |
| 6,764,461 B2 | 7/2004 | Mickley et al. |
| 7,179,251 B2 | 2/2007 | Palasis |
| 7,364,585 B2 | 4/2008 | Weber |
| 7,517,338 B2 | 4/2009 | Freyman et al. |
| 2002/0177772 A1 | 11/2002 | Altman et al. |
| 2003/0055408 A1 | 3/2003 | Dong et al. |
| 2005/0085769 A1 | 4/2005 | MacMahon et al. |

(Continued)

OTHER PUBLICATIONS

International Search Report from PCT/US2011/24839 dated Jun. 30, 2011.

*Primary Examiner* — Bhisma Mehta
(74) *Attorney, Agent, or Firm* — Winthrop & Wienstine, P.A.

(57) ABSTRACT

The invention relates generally to devices and methods for local delivery of therapeutic agents to the wall of a bodily lumen with minimal shearing damage to the therapeutic agents, more specifically to the wall of a blood vessel following atherectomy. A preferred delivery mechanism comprises a balloon, or double balloon, though any distal catheter design may be used to reduce shear stress and to conserve and/or isolate the therapeutic substance.

5 Claims, 8 Drawing Sheets

(56) References Cited

U.S. PATENT DOCUMENTS

| | | |
|---|---|---|
| 2005/0107738 A1 | 5/2005 | Slater et al. |
| 2005/0251106 A1 | 11/2005 | Cervantes et al. |
| 2006/0190022 A1 | 8/2006 | Beyar et al. |
| 2007/0299392 A1 | 12/2007 | Beyar et al. |
| 2008/0077165 A1 | 3/2008 | Murphy |
| 2008/0208310 A1 | 8/2008 | McDermott et al. |
| 2009/0081296 A1 | 3/2009 | Humes et al. |
| 2010/0331817 A1 | 12/2010 | Schaeffer et al. |

DEVICES AND METHODS FOR LOW SHEARING LOCAL DELIVERY OF THERAPEUTIC AGENTS TO THE WALL OF A BODILY LUMEN

BACKGROUND OF THE INVENTION

1. Field of the Invention

The invention relates generally to devices and methods for local delivery of therapeutic agents to the wall of a bodily lumen with minimal shearing damage to the therapeutic agents, more specifically to the wall of a blood vessel following atherectomy. A preferred delivery mechanism comprises a balloon, or double balloon, though any distal catheter design may be used to reduce shear stress and to conserve and/or isolate the therapeutic substance.

2. Description of the Related Art

The present invention overcomes these deficiencies.

BRIEF SUMMARY OF THE INVENTION

Devices and methods for delivery of a single, or more than one, dose of therapeutic agent, including dose(s) of cells and/or drugs that can be varied and controlled without substantial waste. The therapeutic agent, including cells and/or drugs, may be prepositioned at the distal end of the catheter to prevent wasting and promote conservation of the therapeutic agent, to isolate the therapeutic agent, and to reduce shear stress on the therapeutic agent.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1A:
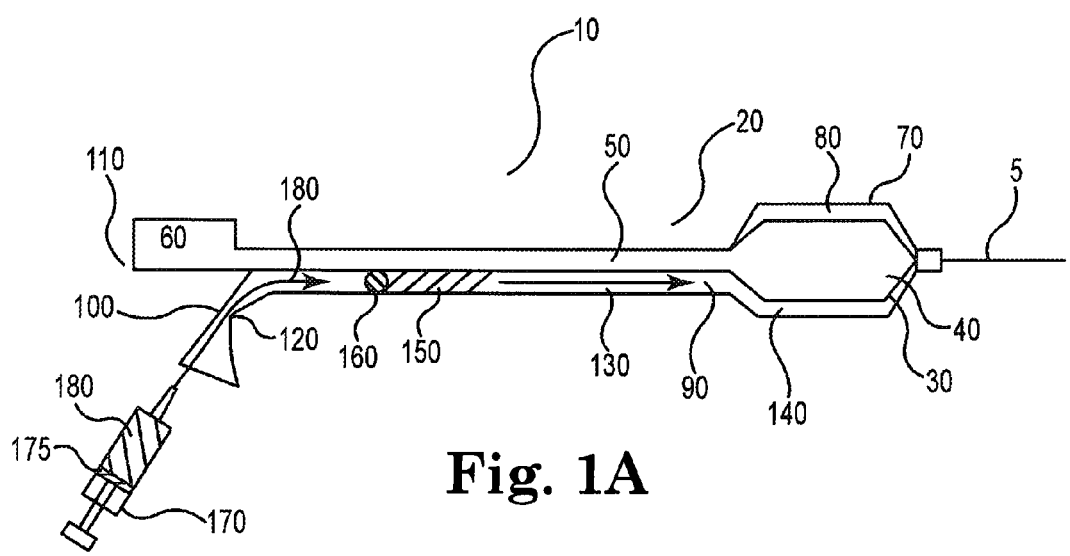
FIG. 1A is a side view of one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

For the purposes of the present invention, the following terms and definitions apply:

"Bodily disorder" refers to any condition that adversely affects the function of the body.

The term "treatment" includes prevention, reduction, delay, stabilization, and/or elimination of a bodily disorder, e.g., a vascular disorder. In certain embodiments, treatment comprises repairing damage cause by the bodily, e.g., vascular, disorder and/or intervention of same, including but not limited to mechanical intervention.

A "therapeutic agent" comprises any substance capable of exerting an effect including, but not limited to therapeutic, prophylactic or diagnostic. Thus, therapeutic agents may comprise anti-inflammatories, anti-infectives, analgesics, anti-proliferatives, and the like including but not limited to antirestenosis drugs. Therapeutic agent further comprises mammalian stem cells. Therapeutic agent as used herein further includes other drugs, genetic materials and biological materials. The genetic materials mean DNA or RNA, including, without limitation, of DNA/RNA encoding a useful protein, intended to be inserted into a human body including viral vectors and non-viral vectors. Viral vectors include adenoviruses, gutted adenoviruses, adeno-associated virus, retroviruses, alpha virus, lentiviruses, herpes simplex virus, ex vivo modified cells (e.g., stem cells, fibroblasts, myoblasts, satellite cells, pericytes, cardiomyocytes, skeletal myocytes, macrophage), replication competent viruses, and hybrid vectors. Non-viral vectors include artificial chromosomes and mini-chromosomes, plasmid DNA vectors, cationic polymers, graft copolymers, neutral polymers PVP, SP1017, lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor .alpha. and .beta., platelet derived endothelial growth factor, platelet derived growth factor, tumor necrosis factor .alpha., hepatocyte growth factor and insulin like growth factor), transcription factors, proteinkinases, CD inhibitors, thymidine kinase, and bone morphogenic proteins. These dimeric proteins can be provided as homodimers, heterodimers, or combinations thereof, alone or together with other molecules.

Therapeutic agents further includes cells that can be of human origin (autologous or allogeneic) or from an animal source (xenogeneic), genetically engineered, if desired, to deliver proteins of interest at the transplant site. Cells within the definition of therapeutic agents herein further include whole bone marrow, bone marrow derived mono-nuclear cells, progenitor cells (e.g., endothelial progenitor cells)

stem cells (e.g., mesenchymal, hematopoietic, neuronal), pluripotent stem cells, fibroblasts, macrophage, and satellite cells.

Therapeutic agent also includes non-genetic substances, such as: anti-thrombogenic agents such as heparin, heparin derivatives, and urokinase; anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as heparin, antithrombin compounds, platelet receptor antagonists, anti-thrombin anticodies, anti-platelet receptor antibodies, aspirin, dipyridamole, protamine, hirudin, prostaglandin inhibitors, platelet inhibitors and tick antiplatelet peptides; vascular cell growth promotors such as growth factors, Vascular Endothelial Growth Factors, growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme, inhibitors including captopril and enalopril. The biologically active material can be used with (a) biologically non-active material(s) including a solvent, a carrier or an excipient, such as sucrose acetate isobutyrate, ethanol, n-methyl pymolidone, dimethyl sulfoxide, benzyl benxoate and benzyl acetate.

Further, "therapeutic agent" includes, in particular in a preferred therapeutic method of the present invention comprising the administration of at least one therapeutic agent to a procedurally traumatized, e.g., by an angioplasty or atherectomy procedure, mammalian vessel to inhibit restenosis. Preferably, the therapeutic agent is a cytoskeletal inhibitor or a smooth muscle inhibitor, including, for example, taxol and functional analogs, equivalents or derivatives thereof such as taxotere, paclitaxel, Abraxane™, Coroxane™ or a cytochalasin, such as cytochalasin B, cytochalasin C, cytochalasin A, cytochalasin D, or analogs or derivatives thereof.

The device of the present invention can be used to apply the biologically active material to any surface of a body lumen where a catheter can be inserted. Such body lumen includes, inter alia, blood vessels, urinary tract, coronary vasculature, esophagus, trachea, colon, and biliary tract.

With reference to the Figures, in general and for all embodiments of the present invention, the device comprises a guide wire 5, an elongated, flexible catheter body 20 having an injection port 100 and an injection lumen 90, whereby at least one therapeutic agent 150 is locally delivered to a lumen for application to the lumen wall. In general, the therapeutic agent(s) is delivered from a delivery mechanism located at or near the distal end of the catheter body, in some embodiments this delivery mechanism comprises a concentric balloon while in others the therapeutic agent(s) is simply delivered into the lumen without aid of a balloon or other delivery mechanism.

In one embodiment, a therapeutic agent delivery device 10 comprising a dual or concentric balloon design is provided. Specifically, a first, inner balloon 30 is provided which may be constructed from a material such as polyethylene which is impermeable. The inner balloon 30 comprises an inner chamber 40 that is connected through an inflation lumen 50 to the proximal end of the catheter to an inflation device 60 for purposes of inflation. This embodiment of the present invention further comprises a second, outer balloon 70 that is generally concentric to the first, inner balloon 30, extending completely around the first, inner balloon 30. This second, outer balloon 70 is constructed from a permeable or selectively permeable material such as a semicroporous ultrafiltration (UF), microfiltration (MF) or dialysis membrane. It is contemplated, however, that various other permeable, microporous or selectively permeable materials. Representative materials for the second, outer balloon may comprise, without limitation, cellulose, cellulose acetate, polyvinyl chloride, polysulfone, polyacrylonitrile, silicon, polyurethanes, natural and synthetic elastomers. Examples of suitable microporous membranes are polyester, polyolefin, a fluoropolymer, or the like having pore sizes of about 1 micron or smaller and preferably from about 10 angstroms to about 1 micron, with a preferred nominal pore size of about 0.05 to 1 micron, but the pore size may be in the range of 0.05 to about 1.5 micron, or 0.05 to about 2 micron.

The second outer balloon 70 comprises a balloon chamber 80 formed between the outer surface of the inner balloon 30 and the inner surface of the outer balloon 70. The balloon chamber is connected to an injection lumen 90 and, through the injection lumen, to the proximal end of the catheter 20 and an injection port 100. The injection lumen 90 is separated from the inflation lumen 50.

Primary purposes of the various embodiments of the present invention include reduction of shearing stress on locally administered therapeutic agents such as drugs and/or cells. Requiring such therapeutic agents to be moved quickly down a long catheter lumen, from the proximal end to the delivery end, in this case a concentric balloon configuration, can damage the therapeutic agents. Further, known solutions require the entire length of the catheter lumen to be filled with the therapeutic agent, a quantity far in excess of the therapeutic dose. This is expensive and wastes a great deal of the therapeutic agent. Moreover, some solutions may attempt to solve the wasting problem by placing a therapeutic dose of the therapeutic agent into the proximal end of the catheter lumen and then attempting to flush the agent through the lumen using saline and the like. This solution introduces air bubbles into the patient lumen and also fails to isolate the therapeutic agent.

To address, inter alia, these issues, the present embodiment provides an injection port 100, located at a manifold 110 disposed at the proximal end of the catheter device 10. The injection port 100 comprises a tapered section 120 which is in fluid communication with the injection lumen 90. The injection lumen 90 comprises a proximal region 130 having a diameter and a distal region also having a diameter 140, wherein the diameter of the proximal region 130 is larger than the diameter of the distal region 140.

Preferably prior to the insertion of the balloon catheter device 10 into the patient, but certainly before the inflation of the inner balloon 30, a therapeutic dose of at least one therapeutic agent 150 is injected into the injection port 100. An isolation plug 160 formed from an inert and inactive material, i.e., a material that is known to not react with the therapeutic agent(s) injected into the injection port 100, is then placed into the injection port 100 and pressured toward the therapeutic agent 150 and into contact therewith at the tapered section 120. The isolation plug 160 may be of any shape and profile or configuration that provides separation and isolation for the therapeutic agent(s) from material or mechanical elements that are placed in the injection lumen proximal to the isolation plug. For example, a ball shape or circular disc shape may be employed. In all cases, the isolation plug 160 comprises a diameter that is slightly less than the diameter of the proximal region of the injection lumen 130, but that is slightly larger than the diameter of the distal region of the injection lumen 140. This allows the isolation plug 160 to be moved through the proximal region of the injection lumen 130, but stops the isolation plug 160 from moving into the distal region of the injection lumen 140. It is at the end of the proximal region 130 and the beginning of the distal region of the injection lumen 140, that the isolation plug 160 is "seated". The pressuring of the isolation plug 160, i.e., the motive force causing the isolation plug 160 to move axially through the injection lumen 90, in particular through the proximal region of the injection lumen 130, is provided by, e.g., a saline injector 170, as illustrated a syringe with a plungeable piston 175 therein for injecting saline 180 into the injection lumen 90. The saline injection pressure is continued to be applied until the isolation plug 160 encounters the distal region of the injection lumen 140 where it is seated as described supra, and the therapeutic agent 150 loads into the balloon chamber 80 which is in fluid communication with the injection lumen 90. Air bubbles that may form between the isolation plug 160 and the therapeutic agent(s) 150 and/or the isolation plug and the saline injection material are eliminated due to the slight clearance between the tapered lumen 120 and the isolation plug 160 which facilitates closer association of the saline injection material 180 with isolation plug 160. Elimination of air bubbles that do form may be facilitated by holding the proximal end of the catheter up above the distal end to allow air to escape through the injection port 100.

The therapeutic agent(s) 150 comprises at least one therapeutic dose, which is, in this embodiment, premeasured before injection into the injection port and subsequent transport to the balloon chamber 80. Once the therapeutic agent(s) 150 is loaded into the balloon chamber 80, the catheter 10 may be inserted into the patient's lumen to the point within the lumen 90 where the therapeutic agent 150 is desired to be applied. Alternatively, the catheter 10 may have been previously inserted before injecting the therapeutic agent(s) 150 into the injection port 170 and loading into the balloon lumen 90. In either case, placement of the outer balloon 70 proximal the application site then allows the operator to inflate the chamber 40 of the inner balloon 30 with standard inflation medium provided through the inflation lumen 50. As a result of inflation of this inner balloon 30, sufficient pressure develops against the balloon chamber 80, and ultimately against the outer balloon 70, to cause the outer balloon to expand, opening the pores or openings therein (not shown) and pressuring or driving or extruding the therapeutic agent(s) 150 through the outer balloon wall 70 pores or openings and onto the surface of the lumen. As is well known in the art, the size and number of pores or openings in the balloon 70 may be tailored to specific therapeutic agent requirements for optimum delivery out of the outer balloon and into the lumen and the vessel wall.

Figure 2:
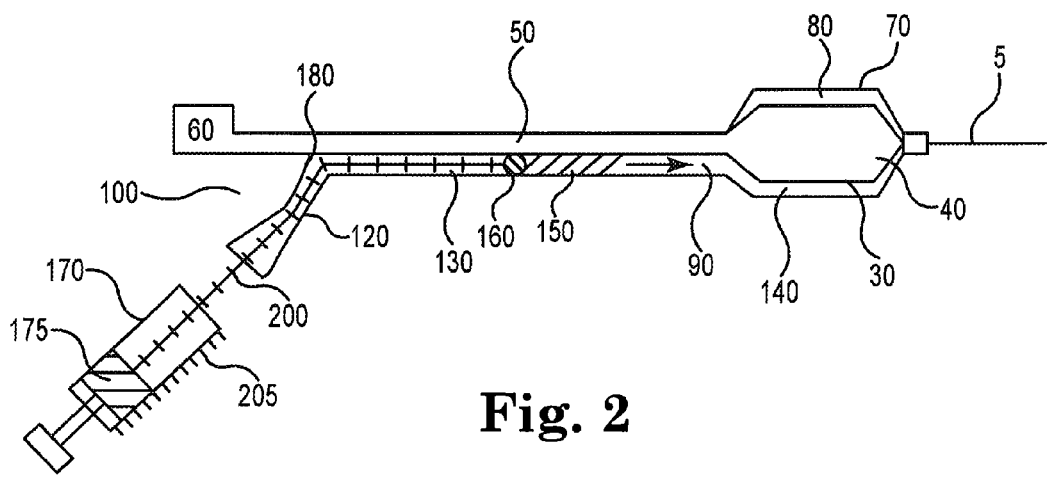
FIG. 2 is a side view of one embodiment of the present invention.

As illustrated in FIG. 2, a second embodiment of the present invention connects the isolation plug 160 with a hollow-bodied syringe 170 having a plungeable piston 175 therein as is known in the art, and operatively connected with isolation plug 160 for pressuring isolation plug 160 and agent (s) 150 distally in lumen 90 and further comprising a marked wire 200, the markings thereon comprising a dosing scale, that is inserted into the injection lumen 90 for pressuring the isolation plug 160 down the injection lumen 90. The marked wire 200 is used to measure the dose amount of the therapeutic agent 150 applied through the balloon pores, the markings thereon corresponding with the dose amount of agent 150 delivered. Alternatively, the syringe 170 may comprise dosing markings 205 thereon for monitoring the amount of agent (s) delivered. This embodiment allows for multiple injections/applications of the therapeutic agent(s) 150 into the lumen 90 and onto the vessel wall. Thus, more than one therapeutic dose of the therapeutic agent(s) 150 may be loaded into the length of the injection lumen 90. The operator is then able to inject the desired amount of therapeutic agent (s) 150 at any point, or points, during the procedure. In this embodiment, it is not necessary to premeasure the therapeutic agent 150 into a therapeutic dose since the operator perceives and controls the amount of therapeutic agent 150 that is actually delivered. As with the embodiment discussed above, once the therapeutic agent 150 is loaded into the balloon chamber 80, inflation of the inner balloon 30, causes the balloon chamber 80 and outer balloon 70 to be sufficiently pressured so that the pores on the outer balloon 70 allow the therapeutic agent(s) 150 to be extruded therethrough and applied to the vessel wall.

Figure 1B:
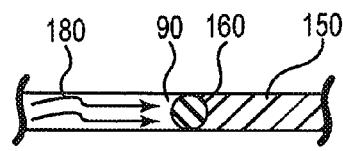
FIG. 1B is a cutaway view of the embodiment of FIG. 1.
Figure 3:
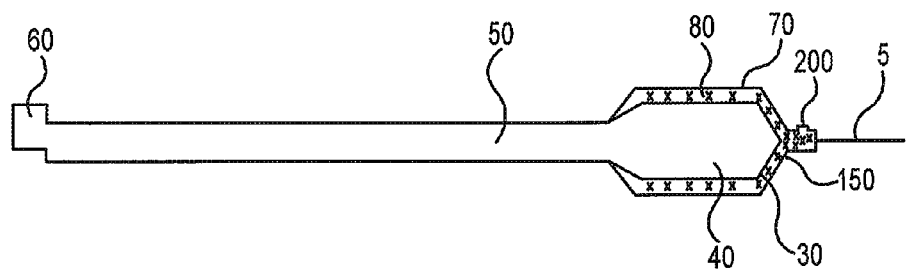
FIG. 3 is a side view of one embodiment of the present invention.

Further embodiments of the present invention seek to further reduce the shear stress on therapeutic agent(s), i.e., cells and/or drugs. As illustrated in FIG. 3, rather than injecting the therapeutic agent into an injection port located at the proximal end of the catheter as in the embodiments of FIGS. 1 and 2, the therapeutic agent 150 is injected into an injection port 200 at the distal end of the catheter. In this embodiment, the injection port 200 is not in fluid communication with the proximal end of the catheter as in FIGS. 1 and 2; instead the distal injection port 200 is in fluid communication with the balloon chamber 80 and injection of the therapeutic agent(s) 150 is sufficient to load the balloon chamber 80. This distal injection port loading method requires injection of the therapeutic agent(s) 150 prior to insertion of the catheter into the patient's vasculature. In this embodiment, injection of the therapeutic agent(s) results in loading of the balloon chamber with the therapeutic agent(s). As with the embodiment discussed above, once the therapeutic agent is loaded into the balloon chamber 80 via distal injection port 200, inflation of the inner balloon 30 via the inflation device 60 which communicates inflation medium down the inflation lumen 50 to inner balloon chamber 40, causes the outer balloon chamber 80 and outer balloon 70 to be sufficiently pressured so that the pores on the outer balloon 70 allow the therapeutic agent(s) 150 to be extruded therethrough and applied to the vessel wall. This embodiment does not require a separate injection lumen.

Figure 4A:
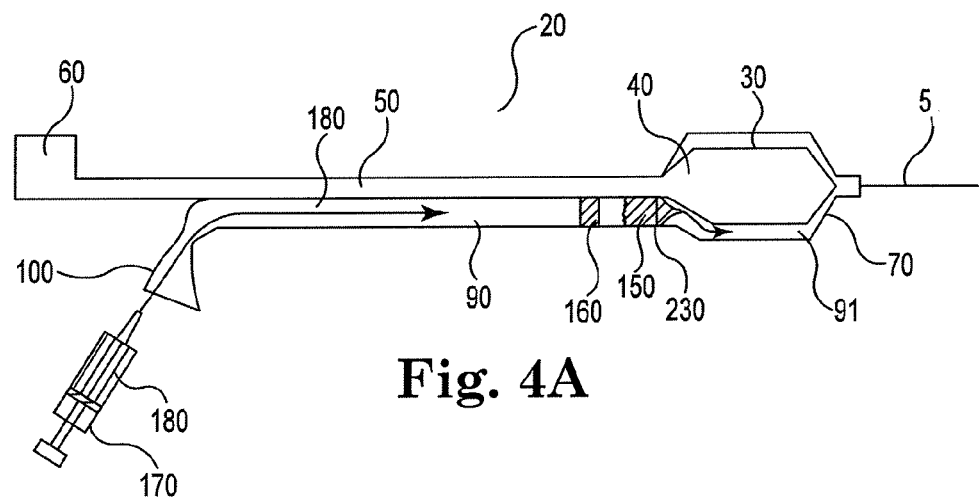
FIG. 4A is a cutaway side view of one embodiment of the present invention.
Figure 4B:
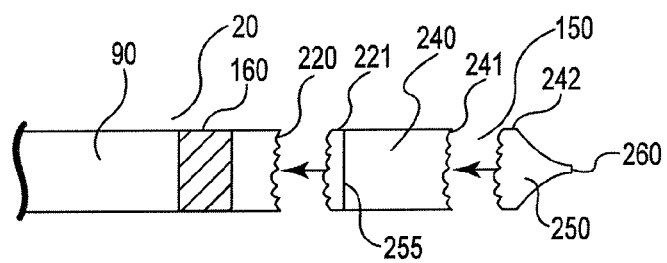
FIG. 4B is a cutaway side view of one embodiment of the present invention.

A further embodiment is shown in FIGS. 4A-4B which seeks to reduce shear stress, reduce waste and provide isolation of the therapeutic agent(s) comprises a catheter 20 comprising an inflation lumen 50 connected with an inflation device 60 for passing inflating medium to the inner chamber 40 therethrough and a distal therapeutic loading lumen 91 formed between the inner balloon 30 and the outer balloon 70. The distal end comprises an isolation plug 160 disposed therein, the isolation plug 160 configured to slidingly move axially distally in response to pressure thereon provided by, e.g., a saline injection using a syringe as shown 170 with saline therein 180 or mechanical means such as a plunger wire actuated by the operator at the proximal end of the catheter. The distal end further comprises a sealing means 220, e.g., threads as illustrated or the equivalent, to accept a therapeutic agent cartridge assembly 230 that is preloaded with a premeasured amount of therapeutic agent 150 in one embodiment. The therapeutic agent cartridge assembly 230 comprises an agent storage section 240 comprising a proximal sealing section 221 which comprises a complementary structure for sealing engagement to sealing means 220. As illustrated, 221 comprises threads so that the seal between 220 and 221 is a threaded, screwed seal though other sealing engagements are well known and within the scope of this invention. Agent storage section 240 also comprises a distal sealing section 241, generally illustrated as a threaded region, capable of connecting with, e.g., threaded connection, the proximal sealing section 242 of the distal cap element 250, also illustrated as threaded, which further comprises a distal outflow lumen 260.

In one embodiment, cartridge assembly 230 comprises a membrane 255 near its proximal end to prevent outflow of agent(s) 150 therefrom. The distal cap element 250 may be screwed off or otherwise unsealed from the agent storage section 240, a measured amount of therapeutic agent(s) 150 placed into the agent storage section 240, the distal cap element 250 replaced, i.e., screwed back into sealing connection with agent storage section 240, connecting distal sealing section 241 with proximal sealing section 242. Then, cartridge assembly 230, preloaded with agent(s) 150 may be sealingly attached to distal end of catheter 20, connecting sealing means 220 with proximal sealing section 221 by, e.g., a threaded sealing connection.

At this point, the device may be inserted into the patient and positioned appropriately, wherein the operator begins pressuring the isolation plug 160 distally down the injection lumen 90 as in previous embodiments using, e.g., saline 180 injected with a syringe 170. The isolation plug 160 will break membrane 255 and begin to pressure the therapeutic agent(s) 150 within cartridge assembly distally to flow out of distal outflow lumen 260 and into balloon chamber 91, thereby loading balloon chamber 91. Thus, inflation of the inner balloon 30 will result in extrusion of the therapeutic agent(s) 150 out of the balloon chamber 91, through the outer balloon 70 and deliver agent(s) 150 into the lumen and apply the agent(s) 150 to the lumen wall.

Figure 4C:
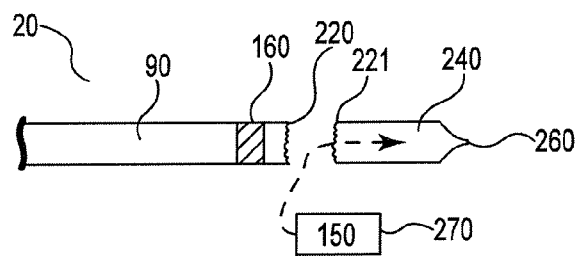
FIG. 4C is a cutaway side view of one embodiment of the present invention.

Thus, the therapeutic agent(s) 150 may be preloaded into the cartridge assembly 230 and the distal end sealed by a membrane 255 to prevent egress therefrom and to preserve the integrity and purity of the therapeutic agent(s) contained therein. Turning now to FIG. 4C, in a different but related embodiment, the therapeutic agent(s) 150 may be encased in a capsule 270 which is either a membrane or a breakable substance as is known in the art. The capsule 270 is placed within agent storage section 240 and then cartridge assembly 230, preloaded with a known, premeasured amount of agent(s) 150 may be sealingly attached to distal end of catheter 20, connecting sealing means 220 with proximal sealing section 221 by, e.g., a threaded sealing connection. Note in this embodiment it is not necessary to have a removeable distal cap 250, though such an element may be present in certain embodiments. Further, since the agent(s) 150 are encased within a capsule 270, it is not necessary to provide a membrane 255 to retain the agent(s) 150. Once the device is loaded with agent(s) 150, the device may be inserted into the patient and positioned appropriately, wherein the operator begins pressuring the isolation plug 160 distally down the injection lumen 90 as in previous embodiments using, e.g., saline 180 injected with a syringe 170. The pressured isolation plug 160 will break capsule 270 and begin to pressure the therapeutic agent(s) 150 within cartridge assembly 230 distally to flow out of distal outflow lumen 260 and into balloon chamber 91, thereby loading balloon chamber 91. Thus, inflation of the inner balloon 30 will result in extrusion of the therapeutic agent(s) 150 out of the balloon chamber 91, through the outer balloon 70 and deliver agent(s) 150 into the lumen and apply the agent(s) 150 to the lumen wall.

Figure 5A:
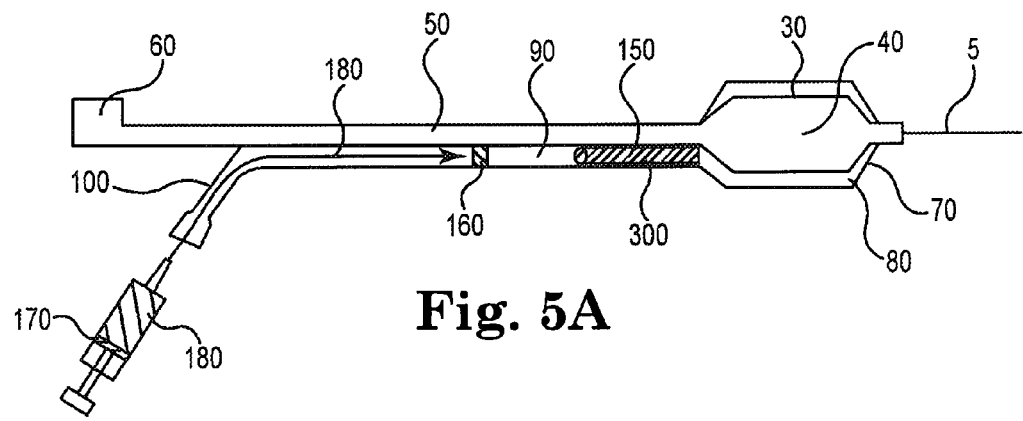
FIG. 5A is a side view of one embodiment of the present invention.
Figure 5B:
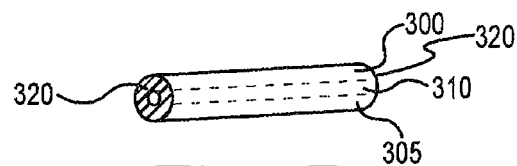
FIG. 5B is a perspective view of one embodiment of a cassette of the present invention.
Figure 6:
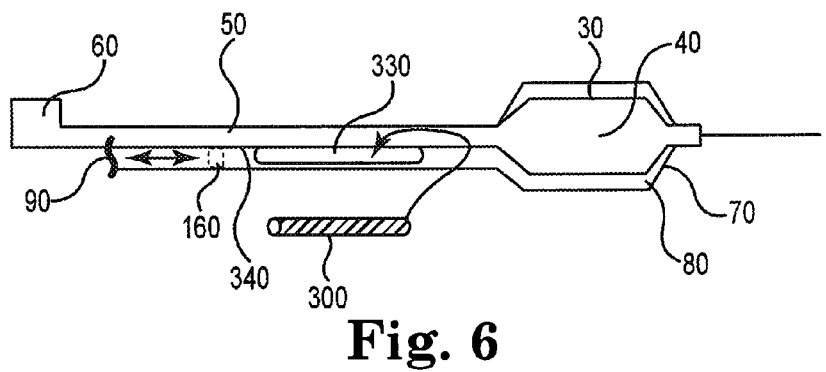
FIG. 6 is a side and partial cutaway view of one embodiment of the present invention.

Turning now to FIGS. 5A-5B and 6, an alternate embodiment comprising a distal therapeutic agent cassette 300 is disclosed which seeks to reduce shear stress and damage, eliminate waste and isolate therapeutic agents. The distal therapeutic agent cassette 300 comprises a flexible polymer tube 305 having a lumen 310 therethrough comprising a diameter and which may be preloaded with a predetermined amount of therapeutic agent(s) 150 and operatively connected with the distal end of the injection lumen 90 and further having a proximal end through which pressure may be applied to cause the therapeutic agent(s) 150 to move out of the cassette 300 and into the balloon chamber 80 wherein the therapeutic agent(s) are loaded and, upon inflation of the inner balloon 30 by actuation of inflation device 60 which sends inflation medium through inflation lumen 50, extruded through the pores of the outer balloon 70. Application of pressure may comprise an isolation plug 160 at the distal end of the catheter as described above which may be moved by a saline 180 injection with a syringe device 170 as illustrated or, alternatively, by a mechanical means such as a wire that is pushed distally through the catheter. The cassette 300 may comprise a membrane seal 320 on proximal and distal ends of the lumen 310 to prevent egress of the therapeutic agent(s) 150 contained therein and to prevent contamination of the agent(s) 150. The membrane seals may be broken by the application of pressure, either by saline 180 pressure and movement of the isolation plug 160 or by mechanical movement of same.

The therapeutic agent 150 may, in this embodiment, comprise a premeasured amount that is preloaded into the cassette 300, wherein the entire amount or dose is delivered within one procedure. Alternatively, multiple therapeutic dosings may be preloaded into the cassette 300 and perceived, measured amounts may be delivered therefrom with aid of the marked, scaled dosing wire 200 and piston 195 described above in relation to FIG. 2 into the balloon chamber 80.

One embodiment of the distal cassette 300 may comprise the injection lumen 90 having a preformed distal seating 330 within which the preloaded cassette 300 is inserted and which may be removably covered by a sheath 340 that is axially moveable, i.e., able to expose and/or cover the installed or inserted cassette 300. The isolation plug 160 may then be pressured distally against the proximal membrane 320, bursting both the proximal and distal membranes 320 and causing the therapeutic agent(s) 150 to flow into the balloon chamber 80 and extruded through the outer balloon 70 on inflation of the inner balloon 30.

Figure 7:
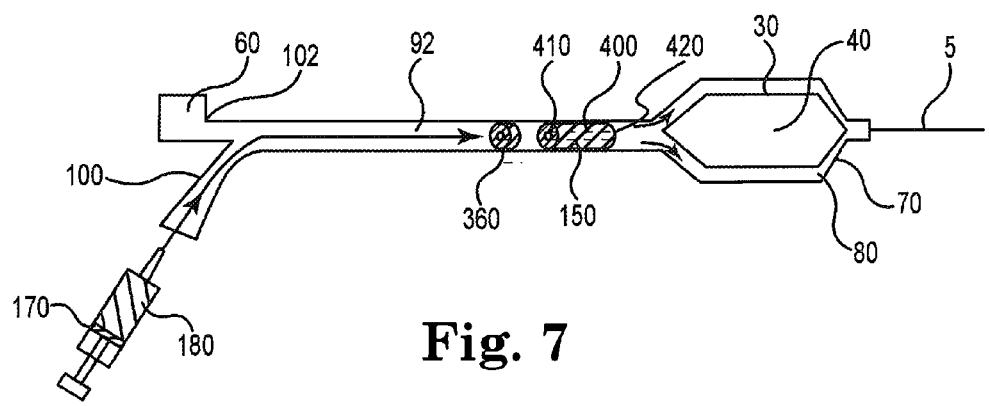
FIG. 7 is a side view of one embodiment of the present invention.

Alternatively, as shown in FIG. 7, a tube-shaped capsule 400, comprising an outer ring 410 holding therapeutic agent(s) 150 therein with a hollow core 420 may be provided within the injection and inflation lumen 92. A membrane material may be disposed on the ends of the capsule's outer ring 410 to hold the therapeutic agent(s) 150 therein. The outer ring 410 is, when the membrane material is broken, in fluid communication with the balloon chamber 80 when pressured and seated distally in lumen 90, while the hollow core 420 is in fluid communication with the inner chamber 40 of inner balloon 30 for inflation of same. The hollow core 420 is not in fluid communication with the balloon chamber 80 nor is the outer ring 410 in fluid communication with the inner chamber 40 of the inner balloon 30 when the capsule 400 is seated. This configuration allows a single lumen 92 to be used to both load the balloon chamber 80 and inflate the inner balloon 30.

A ring-shaped isolation plug 360, having a shape that allows movement through the outer ring 410 of the capsule 400 may be provided to allow distal movement of the therapeutic agent(s) 150 into the balloon chamber 80 for extrusion through the outer balloon 70 upon inflation of the inner balloon 30 and subsequent application to the lumen wall. The ring-shaped isolation plug 360 may be distally moved against the proximal membrane of the capsule 400, ultimately breaking the proximal and distal membranes, causing the agent(s) 150 to flow into the balloon chamber 80 for loading and subsequent application upon inflation of the inner balloon 30. This configuration allows loading of the balloon chamber 80 in a 360-degree fashion, making the operation more efficient, rather than relying on a single inflation lumen and the pressure therein to load the balloon chamber 80 from one side to the other. In this way, a lower pressure may be applied to load the balloon chamber 80, thereby reducing the shear stress on the agent(s) 150. As in previously discussed embodiments, the isolation plug may be pressured forward by aid of a saline injection or by mechanical means including, e.g., a wire which may be marked with dosing values to allow multiple dosings to be given during a procedure.

Once the balloon chamber 80 is loaded, the inner balloon is inflated by inflation device 60 which sends inflation material down the catheter lumen, through the hollow core 420 of capsule 400 and into the inner chamber 40 of the inner balloon. Ultimately, the agent(s) 150 loaded into the balloon chamber 80 are extruded out of the outer balloon 70. Note that this embodiment utilizes a single lumen 92 for inflation and the pressured injection by, e.g., a syringe 170 which injects saline 180 through injection port 100 into lumen 92 and against isolation plug 360. An inflation port 102 connects the inflation device 60 to the lumen 92 for inflating the inner balloon 30.

Figure 8:
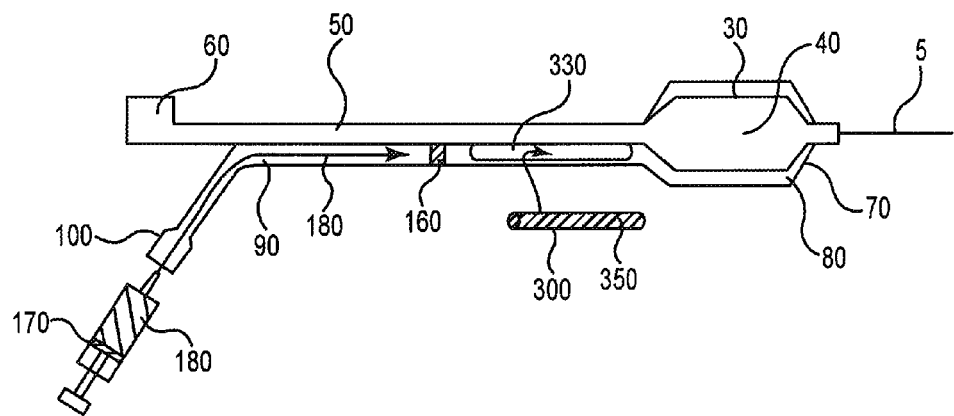
FIG. 8 is a side view of one embodiment of the present invention.

Turning now to FIG. 8, an alternative to the preloaded flexible polymer tube embodiment of the distally loaded cell cassette 300 of FIGS. 5A-5B and 6 is presented which comprises the therapeutic agent(s) as frozen in the shape of the preformed distal seating 330, generally in a cylindrical shape though other shapes will suffice, defined on the distal end of the catheter. A protective and axially slidable sheath as shown in FIG. 6 as element 340 may be disposed thereover in order to close axially over the frozen agent(s) 350 tube to protect the frozen cassette 300 until it is thawed and positioned within the patient. In this embodiment, the frozen therapeutic agents 350 are allowed to thaw within the seating 330 and, when thaw, the isolation plug 160 may then be pressured distally against the now-thawed therapeutic agent(s) 350 by, e.g., a syringe 170 injecting saline 180 into injection lumen 90 and urging the agent(s) 150 to flow into the balloon chamber 80 for extrusion through the outer balloon 70 and application to the lumen wall on inflation of the inner balloon 30 by actuation of inflation device which sends inflation medium through inflation lumen 50 to the inner chamber 40 of inner balloon 30.

Figure 9A:
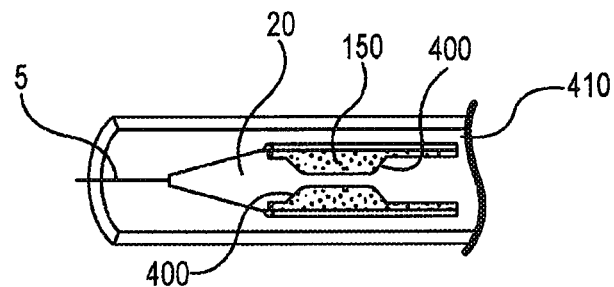
FIG. 9A is a partial cutaway side view of one embodiment of the present invention.
Figure 9B:
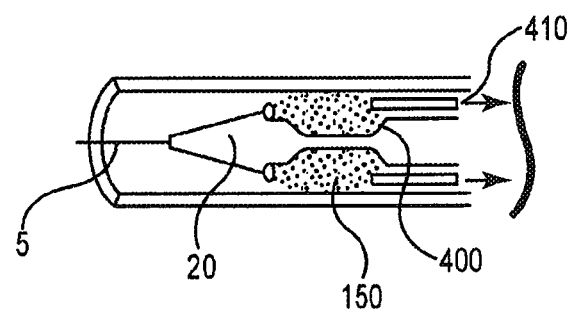
FIG. 9B is a partial cutaway side view of one embodiment of the present invention.
Figure 10A:
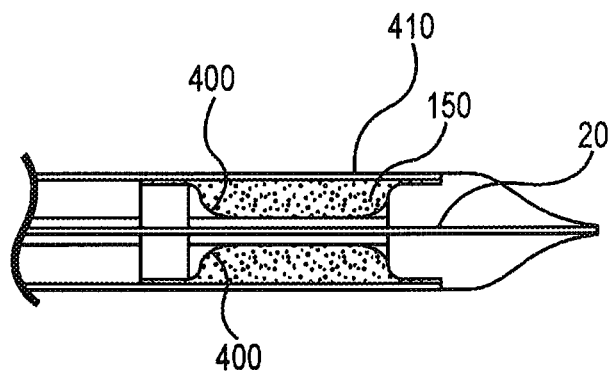
FIG. 10A is a partial cutaway side view of one embodiment of the present invention.
Figure 10B:
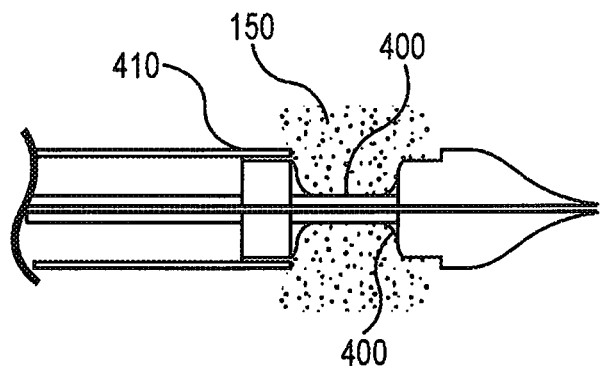
FIG. 10B is a partial cutaway side view of one embodiment of the present invention.

As illustrated in FIGS. 9A-9B and 10A-10B, another embodiment which seeks to reduce shear stress and waste while providing isolation for the therapeutic agent(s) delivered comprises a catheter comprising one or more compartments 400 defined therein and within which may be preloaded premeasured amounts or dosing(s) of therapeutic agent(s) 150 as in FIGS. 9A and 10A. An axially slidable sheath 410 may disposed over the compartment(s) 400 during insertion into the patient's lumen and, when the application site is reached, the sheath 410 may be retracted proximally as in FIGS. 9B and 10B to expose the agent(s) 150 to the lumen. Thus, the agent(s) 150 may migrate to the lumen wall.

Several of the embodiments described herein may be used, as discussed and illustrated, with a concentric balloon delivery mechanism. This delivery mechanism is not, however, the only mechanism by which the various embodiments of the present invention may function to deliver therapeutic agent(s) to the lumen wall. For example, all of the preceding embodiments may eliminate the concentric balloon and simply disperse the therapeutic agent(s) directly into the lumen, rather than causing the agent(s) to flow into a balloon chamber for inflating extrusion therefrom. Though simply dispersing the agent(s) into a lumen may seem inefficient in certain cases, e.g., a high flow rate blood vessel, certain other applications and lumens do not present these difficulties. In these applications, simply exposing the agent(s) to the lumen will suffice to allow migration of the agent(s) to the lumen wall. Each of these non-concentric balloon embodiments are within the scope of the present invention.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A device for loading at least one therapeutic agent into a balloon chamber for application to a patient's lumen wall, comprising an elongated and flexible catheter comprising proximal and distal ends and an inflation lumen and an injection lumen, the injection lumen comprising a proximal region with a diameter and a distal region with a diameter that is less than the diameter of the proximal region;

a substantially concentric pair of balloons disposed on the distal end of the catheter, the substantially concentric pair of balloons comprising an inner balloon having an inner chamber that is in fluid communication with the inflation lumen and an outer balloon comprising pores therethrough and substantially surrounding the inner balloon, the space between the inner balloon and the outer balloon defining a balloon chamber defining the distal region of the injection lumen and having a diameter that is smaller than the diameter of the proximal region of the injection lumen, the balloon chamber in fluid communication with the proximal region of the injection lumen;

an inflation device in operative and fluid communication with the inflation lumen and capable of delivering an inflation medium to the inner chamber of the inner balloon to inflate the inner balloon;

an injection port disposed near the proximal end of the catheter and in fluid communication with the injection lumen and further comprising a tapered section, the injection port allowing injecting access for a therapeutic dose of the at least one therapeutic agent to the injection lumen;

an isolation plug admitted through the injection port after injection of the at least one therapeutic agent, the isolation plug having a diameter that is slightly less than the diameter of the proximal region of the injection lumen and slightly larger than the diameter of the balloon chamber comprising the distal region of the injection lumen, wherein the isolation plug is axially slidable through the injection lumen until reaching the smaller diameter of the balloon chamber at a proximal end of the inner balloon where it is prevented from sliding into the balloon chamber; and a pressuring means for pressuring the isolation plug to slide axially and distally through the injection lumen to the proximal end of the inner balloon, thereby also pressuring the at least one therapeutic agent through the injection lumen and into the balloon chamber where it is loaded in preparation for inflation of the inner balloon and subsequent extrusion of the at least one therapeutic agent out of the balloon chamber, through the outer balloon pores and into the patient's lumen.

2. The device of claim 1, wherein the syringe comprises a saline injection provided by the syringe containing saline.

3. The device of claim 1, wherein the syringe comprises a marked wire in connection with the isolation plug, the wire connected with a plungeable piston and further comprising dosing markings thereon to allow perception and control of the amount of therapeutic agent provided to the balloon chamber, whereby at least one therapeutic dose of the at least one therapeutic agent may be provided to the balloon chamber.

4. The device of claim 1, wherein the isolation plug is formed from a material that is inert and non-reactive with the at least one therapeutic agent.

5. The device of claim 1, wherein the isolation plug comprises a ball shape.

* * * * *